United States Patent
Lackey et al.

(10) Patent No.: US 7,015,231 B2
(45) Date of Patent: Mar. 21, 2006

(54) CHEMICAL COMPOUNDS

(75) Inventors: Karen Elizabeth Lackey, Durham, NC (US); Edgar Raymond Wood, III, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/490,831

(22) PCT Filed: Sep. 24, 2002

(86) PCT No.: PCT/US02/30150

§ 371 (c)(1),
(2), (4) Date: Mar. 25, 2004

(87) PCT Pub. No.: WO03/027111

PCT Pub. Date: Apr. 3, 2003

(65) Prior Publication Data

US 2004/0198766 A1    Oct. 7, 2004

Related U.S. Application Data

(60) Provisional application No. 60/326,012, filed on Sep. 27, 2001.

(51) Int. Cl.
*A61K 31/44* (2006.01)
*C07D 471/00* (2006.01)
(52) U.S. Cl. ..................... 514/300; 546/113
(58) Field of Classification Search ............... 546/113; 514/300
See application file for complete search history.

(56) References Cited

U.S. PATENT DOCUMENTS 5,719,135 A * 2/1998 Buzzetti et al. ............ 514/81
6,268,391 B1   7/2001 Dickerson et al.

FOREIGN PATENT DOCUMENTS

WO   WO 9921859 A1 *   5/1999
WO   00/08202   2/2000

OTHER PUBLICATIONS

Wood et al. Bioorganic & Medicinal Chemistry Letters. 2004. 14:953-957.*

* cited by examiner

*Primary Examiner*—Cecilia Tsang
*Assistant Examiner*—Lexington A. Hoffman
(74) *Attorney, Agent, or Firm*—John L. Lemanowicz

(57) ABSTRACT

The present invention is related to aza-oxindole derivatives, compositions containing the same, and methods of use and manufacture of the same. Such compounds generally are useful pharmacologically as agents in those disease states alleviated by the alteration of mitogen activated signaling pathways in general, and in particular in the inhibition or antagonism of protein kinases, which pathologically involve aberrant cellular proliferation. Such disease states include tumor growth, restenosis, atherosclerosis, pain and thrombosis. In particular, the present invention relates to a series of substituted oxindole compounds, which exhibit Trk family protein tyrosine kinase inhibition, and which are useful in cancer therapy and chronic pain indications.

7 Claims, No Drawings

CHEMICAL COMPOUNDS

This application is filed pursuant to 35 U.S.C. § 371 as a United States National Phase Application of International Application No. PCT/US02/30150 filed Sep. 24, 2002, which claims priority from US 60/326,012 filed Sep. 27, 2001.

BACKGROUND OF THE INVENTION

The present invention is related to aza-oxindole derivatives, compositions containing the same, and methods of use and manufacture of the same. Such compounds generally are useful pharmacologically as agents in those disease states alleviated by the alteration of mitogen activated signaling pathways in general, and in particular in the inhibition or antagonism of protein kinases, which pathologically involve aberrant cellular proliferation. Such disease states include tumor growth, restenosis, atherosclerosis, pain and thrombosis. In particular, the present invention relates to a series of substituted aza-oxindole compounds, which exhibit Trk family protein tyrosine kinase inhibition, and which are useful in cancer therapy and chronic pain indications.

Cell growth, differentiation, metabolism and function are tightly controlled in higher eukaryotes. The ability of a cell to rapidly and appropriately respond to the array of external and internal signals it continually receives is of critical importance in maintaining a balance between these processes (Rozengurt, Current Opinion in Cell Biology 1992, 4, 161–5; Wilks, Progress in Growth Factor Research 1990, 2, 97–111). The loss of control over cellular regulation can often lead to aberrant cell function or death, often resulting in a disease state in the parent organism.

The protein kinases represent a large family of proteins which play a central role in the regulation of a wide variety of cellular processes and maintaining control over cellular function (Hanks, et al., Science 1988, 241, 42–52). A partial list of such kinases includes ab1, ATK, bcr-ab1, Blk, Brk, Btk, c-kit, c-met, c-src, CDK1, CDK2, CDK4, CDK6, cRaf$_1$, CSF1R, CSK, EGFR, ErbB2, ErbB3, ErbB4, ERK, Fak, fes, FGFR1, FGFR2, FGFR3, FGFR4, FGFR5, Fgr, FLK-4, flt-1, Fps, Frk, Fyn, Hck, IGF-1R, INS-R, Jak, KDR, Lck, Lyn, MEK, p38, PDGFR, PIK, PKC, PYK2, ros, tie$_1$, tie$_2$, TRK, Yes, and Zap70.

One of the most commonly studied pathways involving kinase regulation is cellular signaling from receptors at the cell surface to the nucleus (Crews and Erikson, Cell 1993, 74, 215–7). One example of this pathway includes a cascade of kinases in which members of the growth factor receptor tyrosine kinases (such as EGF-R, PDGF-R, VEGF-R, IGF1-R, the Insulin receptor), deliver signals through phosphorylation to other kinases such as Src tyrosine kinase, and the Raf, Mek and Erk serine/threonine kinase families (Crews and Erikson, Cell 1993, 74, 215–7; Ihle, et al., Trends in Biochemical Sciences 1994, 19, 222–7). Each of these kinases is represented by several family members (Pelech and Sanghera, Trends in Biochemical Sciences 1992, 17, 233–8) which play related, but functionally distinct roles. The loss of regulation of the growth factor signaling pathway is a frequent occurrence in cancer as well as other disease states.

A variety of evidence suggests that nerve growth factor (NGF) may be a mediator of some persistent pain states, including neuropathic and inflammatory pain. For example: a) NGF is rapidly elevated in inflamed tissues; b) NGF specific antibodies substantially diminish inflammatory hypersensitivity; c) injection of NGF into adult rats causes a profound hypersensitivity to noxious heat and mechanical stimuli; and d) low level administration of recombinant NGF induces hyperalgesia in healthy humans. NGF produces hyperalgesia through several potential mechanisms. NGF results in the upregulation of peptide neurotransmitters in neurons that detect painful stimuli (nociceptors). NGF increases the excitability of spinal cord neurons to activation. Mast cells express NGF receptors and NGF triggers the release of granules containing histamine and serotonin. Histamine and serotonin are capable of sensitizing nociceptors. (Wood, John (2000) Pathology of Visceral Pain: Molecular Mechanisms and Therapeutic Implications II. Genetic Aproaches to Pain Therapy. Am. J. Physiol. 278(40), G507–G512.)

NGF binds to two different receptors, the neurotrophin receptor p75 (p75NTR) 30 and TrkA. p75NTR is a member of a family of receptors that includes tumor necrosis factor receptor (TNFR) and FAS/APO1. These receptors have in common a cysteine-rich motif in the extracellular domain, a single transmembrane domain, and a cytoplasmic domain. p75NTR signals in a fashion similar to TNFR and FAS via the activation of NFkB, JNK, and ceramide production. The functional significance of p75NTR in NGF mediated biological responses is not clear. Proposed functions include a) modulation of TrkA driven responses and b) induction of cell death in cells that express p75NTR, but not TrkA.

TrkA appears to be the primary mediator of NGF driven biological responses. The most compelling evidence for this comes from NGF and TrkA knockout mice. Mice defective in either the ligand or receptor component of this system have remarkably similar phenotypes. Examples of these phenotypes include severe sensory defects characterized by a complete loss of nociceptive activity and deficiencies in thermoception. Anatomically these mice exhibit extensive peripheral nervous system cell loss in trigeminal, dorsal root, and sympathetic ganglia. Other evidence for the involvement of TrkA in NGF driven responses comes from the study of the PC12 cell line. PC12 cells express high levels of p75NTR and TrkA. NGF causes PC12 cells to differentiate into a neuronal phenotype characterized by the development of axonal projections. Loss of TrkA prevents PC12 cells from differentiating in response to NGF. (Eggert, A. et al (2000) Molecular Dissection of TrkA Signal Transduction Pathways Mediating Differentiation in human Neuroblastoma Cells, *Oncogene*, 19(16), 2043–2051.)

There is evidence that Trk tyrosine kinases play a role in the development of a variety of cancers including, for example, breast and prostate cancer. (Guate, J. L. et al, (1999) Expresion of p75LNGFR and Trk Neurotrophin Receptors in Normal and Neoplastic Human Prostate. *BJU Int* 84(4), 495–502; Tagliabue, E. et al, Nerve Growth Factor cooperates with p185HER2 in Activating Growth of Human Breast Carcinoma Cells, (2000) *J. Biol Chem.* 275(8), 5388–5394.) Further, there is strong evidence that mediation of the Trk kinase signaling will provide beneficial biological effects. (LeSauteur, L et al (1998) Development and Uses of Small Molecule Ligands of TrkA Receptors. *Adv. Behav. Biol.* 49, 615–625; Zhu, Z. et al (1999) Nerve Growth Factor Expression Correlates with Perineural Invasion and Pain in Human Pancreatic Cancer, *Journal of Clinical Oncology*, 17(8), 2419–28; Friess, H. et al, Nerve Growth Factor and its High-Affinity Receptor in Chronic Pancreatitis (1999) *Annals of Surgery* 230(5), 615–24.)

TrkA is a receptor tyrosine kinase that belongs to a subfamily of tyrosine kinases that includes TrkB, and TrkC. TrkB and TrkC are structurally similar to TrkA, but respond to different ligands in the neurotrophin family. NGF signaling through TrkA has been best characterized in the PC12 system and is similar to signal transduction mechanisms of other tyrosine kinase receptors. NGF exists as a homodimer. Binding of NGF promotes dimerization, and autophoshphorylation of TrkA. Phosphorylation of TrkA increases the catalytic activity of the kinase domain and creates binding sites for SH2 domain containing cytoplasmic proteins. SH2 domain binding events initiate the activation of several signal transduction pathways such as PLCg, ras, PI3 kinase/ AKT, and Raf/MEK/ERK. (Frade, J. M. et al, (1998) Nerve growth factor: two receptors, multiple functions, *BioEssays* 20: 137–145; Kaplan, D. R. et al, (1997) Signal transduction by the neurotrophin receptors, *Current Opinion in Cell Biology*. 9: 213–221; Barbacid, M. (1995) Neurotrophic factors and their receptors, *Current Opinion in Cell Biology*. 7:148–155; Snider, W. D. (1994) Functions of the Neurotrophins during nervous system development: What the knockouts are teaching us, *Cell*, 77:627–638.)

The selective inhibition of the Trk family of kinases (TrkA, TrkB, and TrkC) is one aspect of the present invention.

There is a continuing need in the medical field for new and more effective treatments for cancer and for the relief of pain, especially chronic pain. Because TrkA and other Trk kinases may serve as a mediator of NGF driven biological responses, inhibitors of TrkA and other Trk kinases may provide an effective treatment for cancer and for chronic pain states. At present, there is an unmet need for small molecule compounds that may be readily synthesized and are potent inhibitors of TrkA and other Trk family kinases. The present inventors have now discovered novel aza-oxindole derivative compounds that selectively inhibit the catalytic activity of TrkA and/or other Trk family kinases thereby providing new treatment strategies for those afflicted with cancer and chronic pain. It is additionally possible that inhibitors of certain kinases may have utility in the treatment of diseases when the kinase is not misregulated, but is nonetheless essential for maintenance of the disease state.

SUMMARY OF THE INVENTION

In one aspect of the present invention, there is provided compounds of the formula (I):

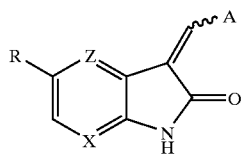

wherein
X is N and Z is CH; or
X is CH and Z is N;
R is hydrogen or halogen; and
A is selected from

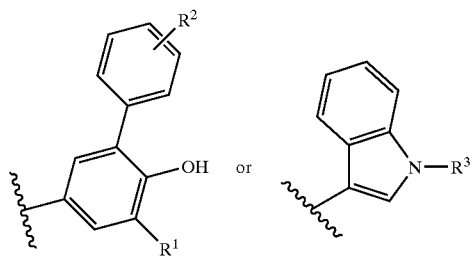

wherein $R^1$ is halogen,
  $R^2$ is hydrogen, $C_1$–$C_6$ alkyl, $C_1$–$C_6$ alkoxy, or $C_1$–$C_6$ alkylsulfanyl, and;
  $R^3$ is hydrogen or $C_1$–$C_6$ alkyl; and
salts, solvates and physiologically functional derivatives thereof.

Due to the presence of an aza-oxindole exocyclic double bond, also included in the compounds of the invention are their respective pure E and Z geometric isomers as well as mixtures of E and Z isomers. The invention as described and claimed does not set any limiting ratios on prevalence of Z to E isomers.

Likewise, it is understood that compounds of formula (I) as used herein includes all tautomeric forms other than the specific tautomer represented by the formula.

Certain of the compounds as described contain one or more chiral, or asymmetric, centers and are therefore capable of existing as optical isomers that are either dextrorotatory or levorotatory. Also included in the compounds of the invention are the respective dextrorotatory or levorotatory pure preparations, and mixtures thereof.

Certain compounds of formula (I) above are optionally provided in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention.

The present invention also provides compounds of formula (I) and pharmaceutically acceptable salts thereof (hereafter collectively referred to as the "active compounds") for use in therapy, and particularly in the treatment of disorders mediated by a kinase, such as TrkA tyrosine kinase, including, for example, cancers and chronic pain. In a further embodiment, the disorder involves abnormal angiogenesis, such as arthritis, diabetic retinopathy, macular degeneration and psoriasis.

A further aspect of the invention provides a method of treating a disorder in a mammal, said disorder mediated by inappropriate mitogen activated kinase activity, including administering to said mammal a therapeutically effective amount of a compound of formula (I) or a salt, solvate, or physiologically functional derivative thereof. In one embodiment, the disorder is cancer. In another embodiment the disorder is chronic pain. In a further embodiment, the disorder involves abnormal angiogenesis, such as arthritis, diabetic retinopathy, macular degeneration and psoriasis.

In a related aspect the present invention comprises a method for inhibiting a kinase comprising bringing said kinase into contact with a compound of formula (I), or a salt, solvate, or physiologically functional derivative thereof.

Another aspect of the present invention provides for the use of a compound of formula (I), or a salt, solvate, or physiologically functional derivative thereof, in the preparation of a medicament for the treatment of a disorder mediated by inappropriate TrkA activity. In one embodiment, the disorder is cancer. In another embodiment, the disorder is chronic pain. In a further embodiment, the disorder involves abnormal angiogenesis, such as arthritis, diabetic retinopathy, macular degeneration and psoriasis.

Additionally, compounds of formula (I) or salts, solvates, or physiologically functional derivatives thereof, can be used in the preparation of a medicament for the treatment of organ transplant rejection, tumor growth, chemotherapy-induced mucositis, radiation-induced mucositis, plantar-palmar syndrome, chemotherapy-induced alopecia, chemotherapy-induced thrombocytopenia, chemotherapy-induced leukopenia and hirsutism or of treating a disease state selected from the group consisting of: mucositis, restenosis, atherosclerosis, rheumatoid arthritis, angiogenesis, hepatic cirrhosis, glomerulonephritis, diabetic nephropathy, malignant nephrosclerosis, chronic obstructive pulmonary disease, thrombotic microangiopathy, aglomerulopathy, psoriasis, diabetes mellitus, inflammation, a neurodegenerative disease, macular degeneration, actinic keratosis and hyperproliferative disorders.

Another aspect of the present invention provides the use of an active compound of formula (I), in co-administration or alternating administration with previously known antitumor therapies for more effective treatment of such tumors.

Other aspects of the present invention related to the inhibition of protein kinases are discussed in more detail below.

The inappropriate TrkA activity referred to herein is any TrkA activity that deviates from the normal TrkA activity expected in a particular mammalian subject. Inappropriate TrkA activity may take the form of, for instance, an abnormal increase in activity, or an aberration in the timing and or control of TrkA activity. Such inappropriate activity may result then, for example, from overexpression or mutation of the protein kinase leading to inappropriate or uncontrolled activation. Furthermore, it is also understood that unwanted TrkA activity may reside in an abnormal source, such as a malignancy. That is, the level of TrkA activity does not have to be abnormal to be considered inappropriate, rather the activity derives from an abnormal source.

DETAILED DESCRIPTION OF THE INVENTION

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Diethanolamine, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydroclloride, Hydroxynaphthoate, Iodide, Isethionate, Lactate, Lactobionate, Laurate, Malate, Maleate, Mandelate, Mesylate, Metaphosphoric, Methylbromide, Methylnitrate, Methylsulfate, Monopotassium Maleate, Mucate, Napsylate, Nitrate, N-methylglucamine, Oxalate, Pamoate (Embonate), Palmitate, Pantethenate, Phosphate/diphosphate, Polygalacturonate, Potassium, Salicylate, Sodium, Stearate, Subacetate, Succinate, Tannate, Tartrate, Teoclate, Tosylate, Trifluoroacetate, Triethiodide, Trimethylammonium and Valerate.

Other salts, which are not pharmaceutically acceptable, may be useful in the preparation of compounds of formula (I) and these form a further aspect of the invention.

Also included within the scope of the invention are the individual isomers of the compounds represented by formula (I) above as well as any wholly or partially equilibrated mixtures thereof. The present invention also covers the individual isomers of the compounds represented by formula above as mixtures with isomers thereof in which one or more chiral asymmetric centers are inverted.

As used herein, the term "lower" refers to a group having between one and six carbons.

As used herein, the term "alkyl" refers to a straight or branched chain hydrocarbon radical having from one to twelve carbon atoms, optionally substituted with substituents selected from the group consisting of $C_1$–$C_6$ alkyl, $C_1$–$C_6$ hydroxyalkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aryl, aryloxy, heteroaryl, aminosulfonyl optionally substituted by alkyl, nitro, cyano, halogen, or $C_1$–$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$–$C_6$ alkyl" refers to an alkyl group as defined above containing at least 1, and at most 6, carbon atoms. Examples of branched or straight chained "$C_1$–$C_6$ alkyl" groups useful in the present invention include, but are not limited to, methyl, ethyl, n-propyl, isopropyl, isobutyl, n-butyl, t-butyl, n-pentyl, and isopentyl.

As used herein, "cycloalkyl" refers to a alicyclic hydrocarbon group with one or more degrees of unsaturation, having from three to twelve carton atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. "Cycloalkyl" includes by way of example: cyclopropyl, cyclobutyl, cyclopentyl, cyclohexyl, cycloheptyl, cyclooctyl, and the like.

As used herein, the term "heterocyclic" or the term "heterocyclyl" refers to a non-aromatic three to twelve-membered heterocyclic ring being saturated or having one or more degrees of unsaturation containing one or more heteroatomic substitutions selected from S, SO, $SO_2$, O or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4dioxane, 1,3-dioxane, piperidine, pyrrolidine, morpholine, tetrahydrothiopyran, tetrahydrothiophene, and the like.

As used herein, the term "aryl" refers to a benzene ring or to an optionally substituted benzene ring system fused to one or more optionally substituted benzene rings to form ring systems such as anthracene, phenanthrene and napthalene, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of aryl include, but are not limited to, phenyl, 2-naphthyl, 1-naphthyl, biphenyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms at any position, where N-oxides and sulfur monoxides and sulfur dioxides are permissible heteroaromatic substitutions, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole and indazole, and the like.

As used herein, the term "alkoxy" refers to the group $R_aO$—, where $R_a$ is alkyl as defined above and the term "$C_1$–$C_6$ alkoxy" refers to an alkoxy group as defined herein wherein the alkyl moiety contains at least 1, and at most 6, carbon atoms. Exemplary $C_1$–$C_6$ alkoxy groups useful in the present invention include, but are not limited to, methoxy, ethoxy, n-propoxy, isopropoxy, n-butoxy, and t-butoxy.

As used herein, the term "alkylsulfanyl" refers to the group $R_aS$—, where $R_a$ is alkyl as defined above and the term "$C_1$–$C_6$ alkylsulfanyl" refers to an alkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl.

As used herein, the term "alkylsulfonyl" refers to the group $R_aSO_2$—, where $R_a$ is alkyl.

As used herein, the term "acyl" refers to the group $R_aC(O)$—, where $R_a$ is alkyl, cycloalkyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, cycloalkyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" is inclusive of circumstances in which described condition is present and circumstances in which the described condition is not present, for example, where the term is used with reference to a chemical substituent, it indicates the inclusion of embodiments in which the specified substituent is present as well as embodiments in which the specified substituent is not present.

As used herein, the term "substituted" indicates the presence of the named substituent or substituents, and includes multiple degrees of substitution.

As used herein, the terms "contain" or "containing" with reference to alkyl or cycloalkyl substituents indicates in-line substitution(s) with one or more substituents at any position along the alkyl or cycloalkyl substituents, such as one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of formula (I)) and a solvent. Such solvents for the purpose of the invention may not interfere with the biological activity of the solute. Solvents may be, by way of example, water, ethanol, or acetic acid.

The compounds of the present invention have the ability to crystallize in more than one form, a characteristic that is known as polymorphism, and such polymorphic forms ("polymorphs") are within the scope of the present invention. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, $5^{th}$ Edition, Vol 1: Principles and Practice, which is incorporated herein by reference to the extent that it teaches physiologically functional derivatives. Including within the scope of the term are the terms "biohydrolyzable carbonate", "biohydrolyzable ureide", "biohydrolyzable carbamate", "biohydrolyzable ester", and "biohydrolyzable amide".

As used herein, the terms "biohydrolyzable carbonate", "biohydrolyzable ureide" and "biohydrolyzable carbamate" include carbonates, ureides, and carbamates, respectively, of a compound of the general formula (I) which carbonates, ureides, and carbamates, do not completely diminish the biological activity of the parent substance. Such carbonates, ureides, and carbamates may confer on the parent compound of the general formula (I) advantageous properties in vivo, such as improved duration of action, onset of action, and the like. Also included are compounds which are relatively biologically inactive but which are converted in vivo by the subject to the biologically active principle. An advantage of such biohydrolyzable forms is that, for example, they facilitate improved oral administration because the carbonates, ureides, and carbamates are more readily absorbed from the gut and are then transformed to a compound of formula (I)

in plasma. Many examples of such biohydrolyzable compounds are known in the art and include, by way of example, lower alkyl carbamates.

As used herein, the term "biohydrolyzable ester" is an ester of a compound of general formula, which does not completely diminish the biological activity of the parent substance. Such esters may confer on the parent compound of the general formula (I) advantageous properties in vivo, such as improved duration of action, onset of action, and the like. Also included are esters which are relatively biologically inactive but which are converted in vivo by the subject to the biologically active principle. An advantage of such biohydrolyzable forms is that, for example, they facilitate improved oral administration because they are more readily absorbed from the gut and are then transformed to a compound of formula (I) in plasma. Many examples of such biohydrolyzable esters are known in the art and include, by way of example, lower alkyl esters, lower acyloxy-alkyl esters, lower alkoxyacyloxyalkyl esters, alkoxyacyloxy esters, alkyl acylamino alkyl esters and choline esters.

As used herein, the term "biohydrolyzable amide" is an amide of a compound of general formula, which does not completely diminish the biological activity of the parent substance. Such amides may confer on the parent compound of the general formula (I) advantageous properties in vivo, such as improved duration of action, onset of action, and the like. Also included are amides which are relatively biologically inactive but which are converted in vivo by the subject to the biologically active principle. An advantage of such biohydrolyzable forms is that, for example, they facilitate improved oral administration because they are more readily absorbed from the gut and are then transformed to a compound of formula (I) in plasma. Many examples of such biohydrolyzable are known in the art and include, by way of example, lower alkyl amides, α-amino acid amides, alkoxyacyl amides and alkylaminoalkylcarbonyl amides.

As used herein, the term "prodrug" includes compounds, which are hydrolyzable in vivo to yield an active compound of formula (I), including for example, biohydrolyzable amides, biohydrolyzable esters and biohydrolyzable carbamates. The term "prodrug" also includes compounds in which the biohydrolyzable functionality is encompassed in the compound of formula (I): for example, a lactam formed by a carboxylic group in $R_1$ and an amine in $R_2$, and compounds which may be oxidized or reduced biologically at a given functional group to yield drug substances of formula (I). Examples of such functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" means a group attached to the compound of formula (I) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An Example of an affinity reagent according to b) would be biotin either directly attached to (I) or linked with a spacer of one to 50 atoms selected from the group consisting of: C, H, O, N, S, or P in any combination. An Example of an affinity reagent according to a) above would be fluorescein, either directly attached to (I) or linked with a spacer of one to 50 atoms selected from the group consisting of: C, H, O, N, S, or P in any combination.

The term "effective amount" means that amount of a drug or pharmaceutical agent that will elicit the biological or medical response of a tissue, system, animal or human that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

As used herein, the term "oxo" refers to the substituent=O.

As used herein, the term "halogen" or "halo" shall include —I (iodo), —Br (bromo), —Cl (chloro) and —F (fluoro).

As used herein, the term "mercapto" refers to the substituent —SH.

As used herein, the term "carboxy" refers to the substituent —COOH.

As used herein, the term "cyano" refers to the substituent —CN.

As used herein, the term "aminosulfonyl" refer to the substituent —SO$_2$NH$_2$.

As used herein, the term "carbamoyl" refers to the substituent —C(O)NH$_2$.

As used herein, the term "sulfanyl" refers to the substituent —S—.

As used herein, the term "sulfenyl" refers to the substituent —S(O)—.

As used herein, the term "sulfonyl" refers to the substituent —S(O)$_2$— or —SO—.

It is to be understood that reference to compounds of formula (I) above, following herein, refers to compounds within the scope of formula (I) as defined above with respect to X, Z, A, R, $R^1$, $R^2$, and $R^3$ unless specifically limited otherwise.

In one embodiment, one of X and Z is nitrogen (N) and the other of X and Z is CH. In one preferred embodiment, X is N and Z is CH. In another preferred embodiment, X is CH and Z is N.

In one embodiment, R is hydrogen, bromo or chloro. In a preferred embodiment, R is hydrogen. In another preferred embodiment, R is bromo or chloro.

In a preferred embodiment, A is

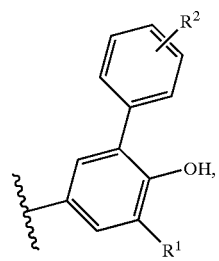

wherein $R^1$ is halo, preferably bromo or chloro, more preferably bromo, and $R^2$ is hydrogen, $C_1$–$C_6$ alkyl, $C_1$–$C_6$ alkoxy, or $C_1$–$C_6$ alkylsulfanyl, preferably $C_1$–$C_6$ alkoxy, more preferably methoxy.

In another preferred embodiment, A is

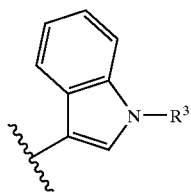

wherein $R^3$ is hydrogen or $C_1$–$C_6$ alkyl, preferably methyl. Highly preferred compounds include:

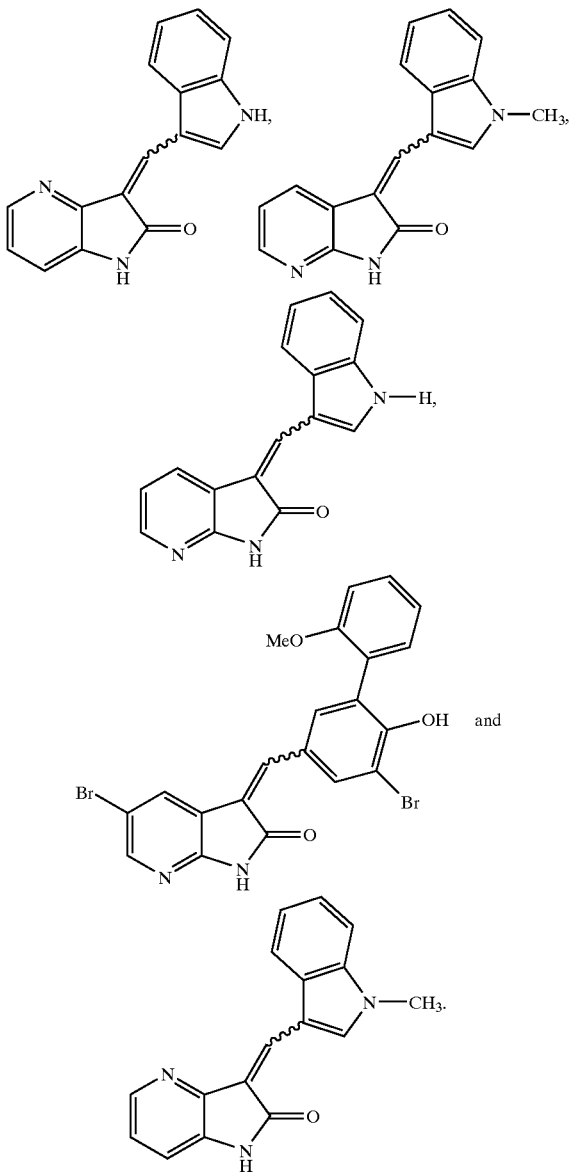

While it is possible that, for use in therapy, therapeutically effective amounts of a compound of formula I, as well as salts, solvates and physiological functional derivatives thereof, may be administered as the raw chemical, it is possible to present the active ingredient as a pharmaceutical composition. Accordingly, the invention further provides pharmaceutical compositions which include therapeutically effective amounts of compounds of the formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula I, or salts, solvates and physiological functional derivatives thereof, with one or more pharmaceutically acceptable carriers, diluents or excipients.

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to about 100 mg/kg of body weight per day, and particularly about 1 to 10 mg/kg of body weight per day. Oral dosage units will generally be administered in the range of from 1 to about 250 mg and more preferably from about 25 to about 250 mg. The daily dosage for a 70 kg mammal will generally be in the range of about 70 mg to 7 grams of a compound of formula I or II.

The dosage to be administered is based on the usual conditions such as the physical condition of the patient, age, body weight, past medical history, route of administrations, severity of the conditions and the like. Oral administration is generally preferred for administration to a human. In some cases, a relatively lower dose is sufficient and, in some cases, a relatively higher dose or increased number of doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. The compounds of the invention can be prepared in a range of concentrations for topical use of about 0.5 to about 5 mg/ml of suitable solvent. A preferred volume for application to the scalp is about 2 ml, resulting in an effective dosage delivered to the patient of about 1 to about 10 mg.

In the methods of the present invention, the compounds herein described in detail can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for Example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing about 0.01 to about 99.5%, more particularly, about 0.5 to about 90% of a compound of the formula (II) in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for Example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

The compounds of formula (I) can be prepared readily according to the following reaction General Synthesis Schemes (in which all variables are as defined herein) and Examples or modifications thereof using readily available starting materials, reagents and conventional synthesis procedures. In these reactions, it is also possible to make use of variants, which are themselves known to those of ordinary skill in this art, but are not mentioned in greater detail.

temperatures ranging from 50–100 C. One may also generate the appropriately substituted benzaldehydes by treating 2-halo-6-substituted phenyl phenols under formylation reaction conditions such as treatment with excess hexamethylenetetramine in a suitable solvent such as acetic acid followed by aqueous acid hydrolysis using, for example, sulfuric acid in water.

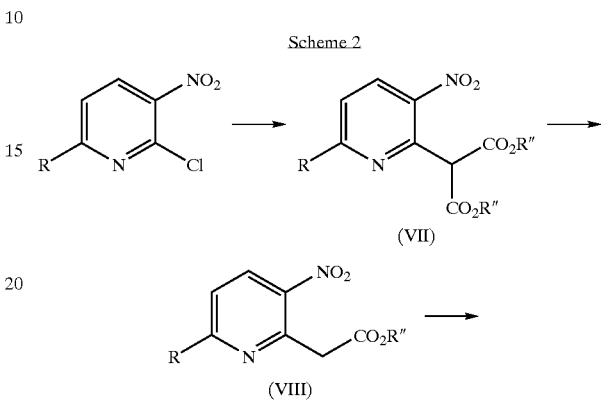

General Synthesis Schemes
Scheme 1

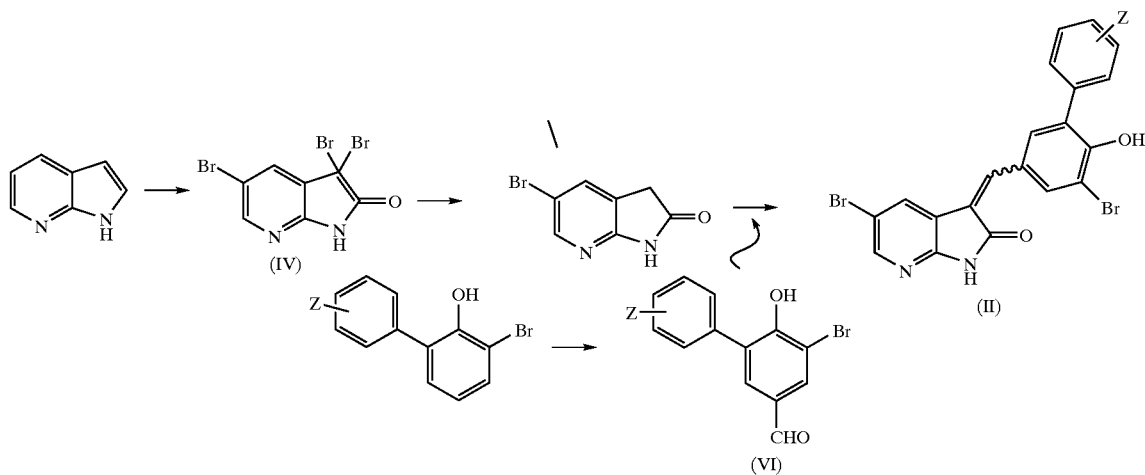

The compounds of the present invention wherein A is a phenyl substituent may be prepared using Scheme 1. Treatment of 7-azaindole with a brominating agent such as Br$_2$ under basic aqueous conditions, which could include using saturated sodium bicarbonate in water, in a suitable solvent such as t-butanol will afford the intermediate compound of formula (IV). The selective reduction of the 3,3-dibromines to afford a compound of formula (V) can be achieved via typical reduction conditions such as treatment with activated zinc in the presence of saturated ammonium chloride in a suitable solvent such as THF. The mixed aldol condensation reaction between a compound of formula (V) and (VI) can be used to afford the desired compound of formula II employing conditions such as treatment with HCl in a suitable solvent such as acetic acid typically at elevated -continued

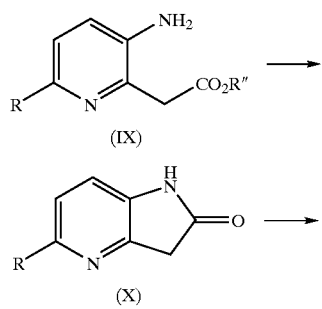

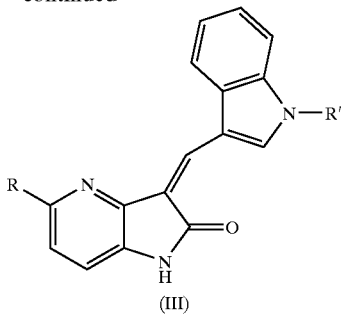

(III)

The compounds of the present invention wherein A is an indole substiuent may be prepared using the synthetic route depicted in Scheme 2. 2-Chloro-3-nitropyridine can be used as the starting material to generate a compound of formula (VII) by treatment with the anion of a dimalonate, for example, diethylmalonate prepared using a strong base such as sodium hydride in a suitable solvent such as DMSO. Treatment of a compound of formula (VII) under decarboxylation conditions such as LiCl in a suitable solvent such as water and DMSO may generate the intermediate compound of formula (VIII). The reduction of a compound of formula (VIII) to generate a compound of formula (IX) may be carried out under multiple conditions, but, by way of example, one could employ an atmosphere of $H_2$ under 40 psi of pressure in the presence of a catalytic amount of Pd on carbon in a suitable solvent such as ethanol. The "R" groups can be incorporated in the beginning of the synthesis, or alternatively, one could introduce substitution using the intermediate compound of formula (Xa) where R=H in (X). Scheme 3 depicts a sequence of reactions to introduce a bromine in the 5-position of the 4-aza-oxindole ring system. One skilled in the art may accomplish this readily using a bromination reaction such as $Br_2$ under basic aqueous conditions, which could include using saturated sodium bicarbonate in water, in a suitable solvent such as t-butanol will afford the intermediate compound of formula (XI). The selective reduction of the 3,3-dibromines to afford a compound of formula (Xb) can be achieved via typical reduction conditions such as treatment with activated zinc in the presence of saturated ammonium chloride in a suitable solvent such as THF. The mixed aldol condensation reaction between a compound of formula (X) and a substituted indole-3-carboxaldehyde can be used to afford the desired compound of formula (III) employing conditions such as treatment with HCl in a suitable solvent such as acetic acid typically at elevated temperatures in a range of 50–100C.

Scheme 3

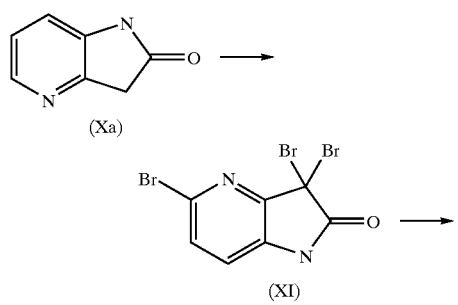

-continued

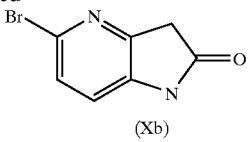

(Xb)

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:

| | |
|---|---|
| g = | grams |
| mg = | milligrams |
| L = | liters |
| mL = | milliliters |
| M = | molar |
| N = | normal |
| mM = | millimolar |
| i.v. = | intravenous |
| p.o. = | per oral |
| s.c. = | subcutaneous |
| Hz = | hertz |
| mol = | moles |
| mmol = | millimoles |
| mbar = | millibar |
| psi = | pounds per square inch |
| rt = | room temperature |
| min = | minutes |
| h = | hours |
| mp = | melting point |
| TLC = | thin layer chromatography |
| $R_f$ = | relative TLC mobility |
| MS = | mass spectrometry |
| NMR = | nuclear magnetic resonance spectroscopy |
| APCI = | atmospheric pressure chemical ionization |
| ESI = | electrospray ionization |
| m/z = | mass to charge ratio |
| $t_r$ = | retention time |
| Pd/C = | palladium on activated carbon |
| ether = | diethyl ether |
| MeOH = | methanol |
| Tert-BuOH = | tert-butyl alcohol |
| EtOAc = | ethyl acetate |
| TEA = | triethylamine |
| DIEA = | diisopropylethylamine |
| THF = | tetrahydrofuran |
| DMF = | N,N-dimethylformamide |
| DMSO = | dimethylsulfoxide |
| DDQ = | 2,3-dichloro-5,6-dicyano-1,4-benzoquinone |
| LAH = | lithium aluminum hydride |
| TFA = | trifluoroacetic acid |
| LDA = | lithium diisopropylamide |
| THP = | tetrahydropyranyl |
| NMM = | N-methylmorpholine, 4-methylmorpholine |
| HMPA = | hexamethylphosphoric triamide |
| DMPU = | 1,3-dimethypropylene urea |
| d = | days |
| ppm = | parts per million |
| kD = | kiloDalton |
| LPS = | lipopolysaccharide |
| PMA = | phorbol myristate acetate |
| SPA = | scintillation proximity assay |

| | |
|---|---|
| EDTA = | ethylenediamine tetraacetic acid |
| FBS = | fetal bovine serum |
| PBS = | phosphate buffered saline solution |
| BrdU = | bromodeoxyuridine |
| BSA = | bovine serum albumin |
| FCS = | fetal calf serum |
| DMEM = | Dulbeccols modified Eaglels medium |
| pfu = | plaque forming units |
| MOI = | multiplicity of infection |

Reagents are commercially available or are prepared according to procedures in the literature. The physical data given for the compounds exemplified is consistent with the assigned structure of those compounds. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

EXAMPLE 1

Preparation of 3-(3-Bromo-4-hydroxy-5-(2'methoxyphenyl)-benzylidene)-5-bromo-1,3-dihydro-pyrrolo[2,3-b]pyridin-2-one

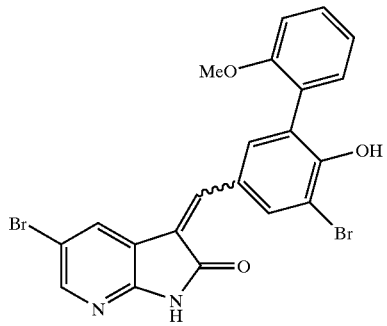

a: Synthesis of 5-Bromo-7aza-oxindole

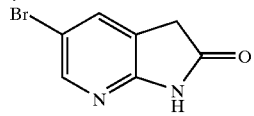

i: 3,3-Dibromo-7-azaoxindole

A solution of 7-azaindole (4.0 g, 34 mmol) in tert-BuOH (200 mL) is stirred at room temperature and pyridinium perbromide (32.5 g, 0.1 mol) is added in portions over 30 min. and the reaction mixture is stirred for 3 h. Pyridinium perbromide (10.8 g, 33 mmol) is added and the mixture is stirred for a further 2 h. The tert-BuOH is evaporated under educed pressure and the residue is partitioned between water (300 mL) and EtOAc (300 mL). The organic layer is separated and the aqueous layer is extracted with EtOAc. The combined organic layers are washed with water (2×50 mL), and brine. The organic layer is dried over anhydrous MgSO$_4$, filtered and the solvent evaporated. Trituration of the residue with CH$_2$Cl$_2$ gives a white solid which is collected by filtration and dried under vacuum to give 3,3-dibromo-7-azaoxindole, 8.35 g. $^1$H NMR (d$^6$ DMSO) 11.99 (s, 1H), 8.21 (dd, 1H, J=5.1, 1.5 Hz), 8.00 (dd, 1H J=7.5, 1.5 Hz), 7.17 (dd, 1H, J=7.5, 5.1 Hz). MS (+ve ES) 293 (28), (M+H), 147 (100).

ii: 3,3,5 Tribromooxindole

A solution of 3,3-dibromo-7-azaoxindole (5.0 g, 13.4 mmol) in tert-BuOH (100 mL) and water (100 mL) is stirred at room temperature and bromine (5.5 g, 34.3 mmol) is added dropwise over 20 min. A saturated aqueous solution of sodium bicarbonate (approx. 15 mL) is added dropwise over 30 min to raise the pH of the solution to 6.5. The yellow solid formed is collected by filtration. The filtrate is condensed to approx. 100 mL and extracted with CHCl$_3$ (2×50 mL). The combined organic extracts are dried over anhydrous magnesium sulfate and the solvent is evaporated under reduced pressure to leave a yellow solid. The solids are combined and dried under vacuum to give 3,3,5 tribromooxindole as a yellow solid, 6.25 g (98%). $^1$H NMR (CDCl$_3$) δ 9.4 (br s, 1H), 8.28 (d, 1H, J=2 Hz), 7.95 (d, 1H, J=2 Hz).

iii: 5 Bromo-7-azaoxindole

A solution of 3,3,5 tribromooxindole (5.0 g, 13.4 mmol) in fresh THF (100 mL) is stirred at room temperature and a saturated aqueous solution of ammonium chloride (100 mL) is added. The flask is placed in a water bath and activated zinc dust (15.0 g, 230 mmol) is added. The mixture is stirred for 20 min and the zinc is removed by filtration through a pad of diatomaceous earth. The organic layer is separated and the aqueous layer is extracted with THF (20 mL). The combined organic layers were washed with saturated brine solution, dried over anhydrous magnesium sulfate and the solvent removed under reduced pressure. The brown residue is triturated with water (20 mL) and the tan solid is collected by filtration and dried under vacuum to give 5-bromo-7-azaoxindole as a tan solid, 2.02 g (71%). $^1$H NMR (d$^6$ DMSO) δ 11.13 (s, 1H), 8.15 (s, 1H), 8.76 (s, 1H), 3.57 (s, 2H). MS (AP −ve) 211 (100) (M−H).

b: Synthesis of 3-(3-Bromo-4-hydroxy-5-(2'methoxyphenyl)-benzylidene)-5-bromo-1,3-dihydro-pyrrolo[2,3-b]pyridin-2-one A mixture of 0.050 g (0.17 mmol) of 5-bromo-7-azaoxindole and 0.061 g (0.20 mmol) of 3-bromo-4-hydroxy-5-(2'methoxyphenyl)-hydroxybenzaldehyde (prepared according to the general procedure in Scheme 1: $^1$H NMR (DMSO-d$_6$): δ 9.84 (s, 1H); 8.08 (s, 1H); 7.73 (s, 1H); 7.5 (bs, 1H); 7.48 (t, 1H); 7.30 (d, 1H); 7.11 (t, 1H); 7.06 (dd, 1H); 3.89 (s, 3H), APCI 305 (MH+)) was stirred in 1 ml of HOAc. Concentrated HCl (0.50 mL) was added and the mixture was heated to 80° C. for 2 hrs. After cooling to ambient temperature the reaction mixture was diluted with EtOAc. The solid was collected by vacuum filtration and washed with EtOAc and Et$_2$O to yield 3-(3-Bromo-4-hydroxy-5-(2'methoxyphenyl)-benzylidene)-5-bromo-1,3-dihydro-pyrrolo[2,3-b]pyridin-2-one as a yellow solid (0.073 g, 73%): $^1$H NMR (DMSO-d$_6$): δ 11.39 (bs, 1H); (s, 1H); 8.25 (s, 1H); 8.19 (s, 1H); 8.11 (s, 1H); 7.95 (s, 1H); 7.42 (m, 2H); 7.23 (m, 2H); 7.10 (m, 2H); 3.93 (s, 3H). APCI (−ve) 501 (M−H).

EXAMPLE 2

Preparation of (3Z)-3-[(1-methyl-1H-indol-3-yl)methylene]-1,3-dihydro-2H-pyrrolo[3,2-b]pyridin-2-one

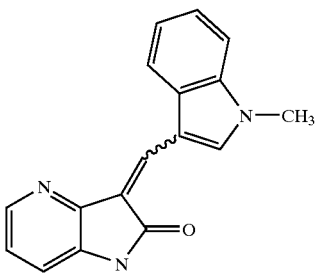

a: Synthesis of 4-aza-oxindole

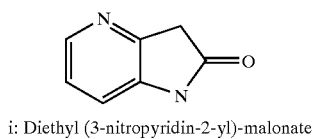

i: Diethyl (3-nitropyridin-2-yl)-malonate

Sodium hydride (60% dispersion in oil, 5.57 g, 0.14 mol) was carefully washed with hexanes under nitrogen before the addition of DMSO (115 mL). Diethyl malonate (22.3 g, 0.14 mol) was added dropwise over 20 min and the mixture was stirred for an additional 30 min at room temperature. 2-Chloro-3-nitropyridine (10 g, 0.06 mol) was added to the reaction and the reaction was placed in a pre-heated oil bath set to 100° C. for 15 min. The reaction was cooled to room temperature and poured into aqueous ammonium chloride (saturated solution, 150 mL). The aqueous solution was extracted with EtOAc:Hexanes (1:1) four times (200 mL each) and the organic layers were combined. The organics were concentrated to afford a solid that was recrystallized from a minimal amount of EtOAc:Hexanes (1:1) (12.5 g, 70% yield). APCI MS m/z 281 (M−1).

ii: Ethyl 2-(3-nitro-pyridin-2-yl)-acetate

Diethyl (3-nitropyridin-2-yl)-malonate (12.5 g, 0.044 mol) was dissolved in DMSO (150 mL) and water (0.79 mL, 0.044 mol) and lithium chloride (4.65 g, 0.11 mol) were added at room temperature under nitrogen. The reaction was warmed to 100° C. 12 h and more lithium chloride (1 g) was added to the reaction. The reaction was heated for another 5 hours and cooled to room temperature. Brine (150 mL) was added to the reaction before extracting with EtOAc (3×, 275 mL each). The organics were combined and dried over sodium sulfate, then concentrated in vacuo. The resulting residue was triturated with diethyl ether and collected by filtration (8.6 g, 92% yield). 1H NMR 400 MHz (DMSO-d6) 8.83 (m, 1H); 8.53 (m, 1H); 7.65 (m, 1H); 4.23 (s, 2H); 4.07 (m, 2H); 1.16 (m, 3H).

iii: Ethyl 2-(3-amino-pyridin-2-yl)-acetate

Under an atmosphere of nitrogen, Pd/C (10%, 1.36 g) was charged to a round bottome flask. Ethyl 2-(3-nitro-pyridin-2-yl)-acetate (8.6 g, 0.41 mol) was dissolved in ethanol (200 mL) and added to the reaction vessel. The reaction was placed under an atmosphere of hydrogen and stirred at room temperature for 30 min. The reaction was filtered through celite and the filtrate was concentrated in vacuo to afford the product as a tan solid (6.94 g, 94% yield).

iv: 4-azaoxindole

Ethyl 2-(3-amino-pyridin-2-yl)-acetate (6.94 g, 0.038 mol) was dissolved in diethyl ether (100 mL) at room temperature. Hydrochloric acid (2M, 35 mL) was added and the reaction was stirred for 30 minutes. The volatiles were removed to afford a brown solid that was re-crystallized from ethanol and diethyl ether (4.0 g, 62% yield). 1H NMR 400 MHz (DMSO-d6) 12.35 (s, 1H); 8.12 (m, 1H); 7.90 (m, 1H); 7.14 (m, 1H); 5.75 (s, 2H). Electrospray MS m/z 135 (M+1).

b: Synthesis of (3Z)-3-[(1-methyl-1H-indol-3-yl)methylene]-1,3-dihydro-2H-pyrrolo[3,2-b]pyridin-2-one 1-Methylindole carboxaldehyde (0.020 g, 0.15 mmol), 4-aza-oxindole (0.024 g, 0.15 mmol), acetic acid (1.5 mL) and concentrated HCl (0.4 mL) were combined at room temperature and then warmed to 40 C for 16 hours. Ethyl Acetate (10 mL) was added after the reaction was cooled to room temperature and the reddish orange solid that persisted was collected by filtration. The solids were dried in a vacume oven set to 70 C for 22 hours, which afforded an orange solid (0.029 g, 70% yield). 1H NMR 400 MHz (DMSO-d6) 8:1 mixture of isomers. 11.39 A(s, 1H), 10.54 B(s,1H), 9.98 B(s,1H), 9.69 A(s, 1H), 9.30 A(s, 1H), 8.28 A(m, 1H) 8.28 B(m, 1H), 8.23 A(d, 1H), 8.02 B(s, 1H), 7.95 B(d, 1H), 7.67 A(m, 1H), 7.63 A(m, 1H), 7.63 B(m, 1H), 7.48 A(m, 1H), 7.42 A(m, 2H), 7.32B(m, 1H), 7.20 B(m, 1H), 7.16 B(m, 1H), 4.03 A(s, 3H), 3.99 B(s, 3H). Electrospray MS m/z 276 (M+1).

Example 3: (3Z)-3-[(1H-indol-3-yl)methylene]-1,3-dihydro-2H-pyrrolo[3,2-b]pyridin-2-one

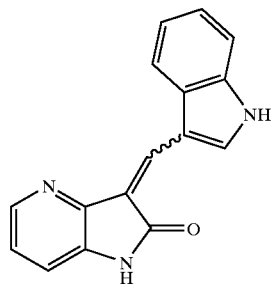

Prepared in an analogous method to Example 2, except indole carboxaldehyde was used in place of 1-methylindole carboxaldehyde. Electrospray MS m/z 262 (M+1).

Example 4: 3-[(1-methyl-1H-indol-3-yl)methylene]-1,3-dihydro-pyrrolo[2,3-b]pyridin-2-one

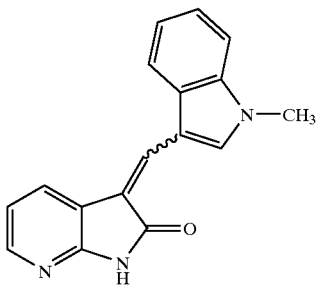

Prepared in an analogous method to Example 2, except 7-aza-oxindole was used in place of 4-aza-oxindole. Electrospray MS m/z 276 (M+1).

Example 5: 3-[(1H-indol-3-yl)methylene]-1,3-dihydro-pyrrolo[2,3-b]pyridin-2-one

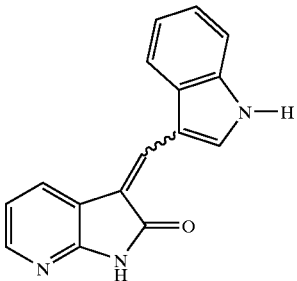

Prepared in an analogous method to Example 2, except 7-aza-oxindole was used in place of 4-aza-oxindole and indole carboxaldehyde was used in place of 1-methylindole carboxaldehyde. Electrospray MS m/z 262 (M+1).

Biological Data

The compounds of the present invention have valuable pharmacologic properties. Different compounds from this class are particularly effective at inhibiting the trkA kinase enzyme at concentrations that range from 0.0001 to 1 $\mu$M and additionally show specificity relative to other kinases. Substrate phosphorylation assays were carried out as follows:

Screening format: Tyrosine kinase activity is being measured using a synthetic peptide substrate. The enzyme is a GST-fusion of the intracellular domain expressed in SF9 cells. The enzyme is expressed and purified by Regeneron. The enzyme is preincubated with cold ATP and Mg to allow autophosphorylation prior to running the screen. This increases the initial rate of catalysis approximately 3 fold. The assay is performed in 96 well microtitre plates, and reaction products are detected following filtration through millipore p81 phosphocellulose plates.

Assay Conditions

| Peptide substrate | Src peptide, NH2- RRRAAAEEIYGEI- NH2 |
| --- | --- |
| Peptide Km | 60 uM |
| ATP Km | 30 uM |
| Kcat/Km (peptide): | $1 \times 10^4$ |
| Assay conditions | 20–40 nM TrkA, 30 uM ATP, 50 uM Src peptide, 50 mM MOPS pH 7.5, 10 mM $MgCl^2$, 0.6 uCi $^{33}P\square ATP$ |
| Incubation | RT for 120' |
| Termination | Add 100 ul of 0.5% Phosphoric acid. Spot 100 ul onto millipore p81 96 well filter plate. Filter, wash 3x with 200 ul 0.5% phosphoric acid. Add 50 ul scintillation cocktail. Count in Packard Topcount |

Representative results are shown in Table 1 for the TrkA tyrosine kinase inhibition

TABLE 1

| Example | Substrate Phosphorylation TrkA |
| --- | --- |
| 1 | +++ |
| 2 | +++ |
| 3 | ++ |
| 4 | +++ |
| 5 | +++ |

| $IC_{50}$ values | Symbol |
| --- | --- |
| <0.010 uM | +++ |
| 0.010–0.25 uM | ++ |
| 0.25–2.5 uM | + |
| >2.5 uM | − |
| Not determined | ND |

Utility of Invention

Inhibitors of Trk tyrosine kinase have utility as agents in the treatment of a wide variety of disorders. These include, for example, cancers and chronic pain.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims, which follow, and that such claims be interpreted as broadly as is reasonable.

The application of which this description and claim(s) forms part may be used as a basis for priority in respect of any subsequent application. The claims of such subsequent application may be directed to any feature or combination of features described herein. They may take the form of product, formulation, process or use claims and may include, by way of example and without limitation, one or more of the following claim(s).

We claim:

1. A compound of the formula (I):

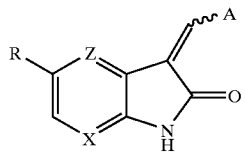

wherein
X is CH and Z is N;
R is hydrogen or halogen; and
A is selected from

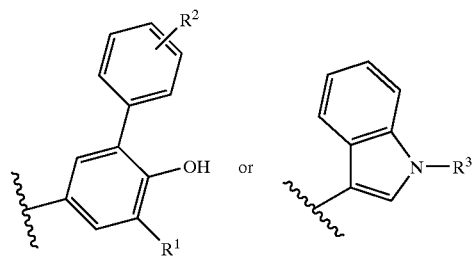

wherein R¹ is halogen,
R² is hydrogen, $C_1$–$C_6$ alkyl, $C_1$–$C_6$ alkoxy, or $C_1$–$C_6$ alkylsulfanyl, and;
R³ is hydrogen or $C_1$–$C_6$ alkyl; or
salts or solvates thereof.

2. A compound as claimed in claim 1, wherein R is hydrogen, bromo or chloro.

3. A compound as claimed in claim 1, wherein A is,

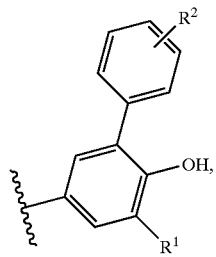

and R¹ is halogen and R² is hydrogen, $C_1$–$C_6$ alkyl, $C_1$–$C_6$ alkoxy, or $C_1$–$C_6$ alkylsulfanyl.

4. A compound as claimed in claim 1, wherein A is,

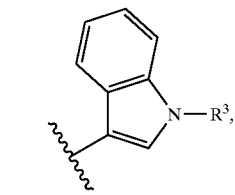

wherein R³ is hydrogen or $C_1$–$C_6$ alkyl.

5. A compound selected from:

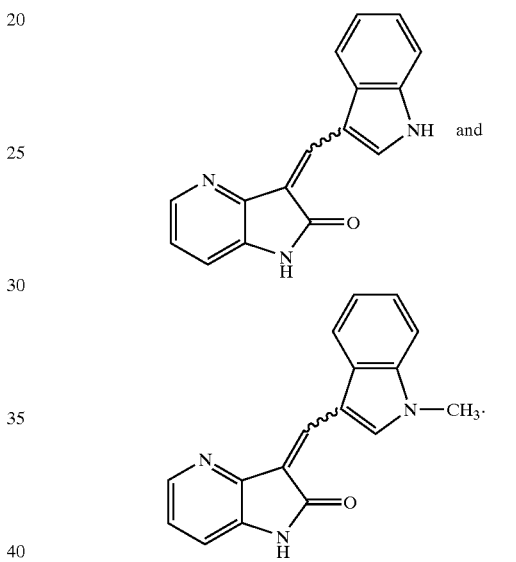

6. The compound:
(3Z)-3-[(1-methyl-1H-indol-3-yl)methylene]-1,3-dihydro-2H-pyrrolo[3,2-b]pyridin-2-one or salts or solvates thereof.

7. The compound:
(3Z)-3-[(1H-indol-3-yl)methylene]-1,3-dihydro-2H-pyrrolo[3,2-b]pyridin-2-one or salts or solvates thereof.

* * * * *